United States Patent [19]

Blades

[11] 4,252,792

[45] Feb. 24, 1981

[54] INJECTABLE RABIES VACCINE COMPOSITION AND METHOD FOR PREPARING SAME

[75] Inventor: James E. Blades, Kansas City, Mo.

[73] Assignee: Douglas Industries, Inc., Lenexa, Kans.

[21] Appl. No.: 77,498

[22] Filed: Sep. 21, 1979

Related U.S. Application Data

[63] Continuation of Ser. No. 971,091, Dec. 19, 1978, abandoned.

[51] Int. Cl.$^3$ .......................................... A61K 39/205
[52] U.S. Cl. .................................... 424/89; 435/235; 435/238
[58] Field of Search .......................................... 424/89

[56] References Cited

FOREIGN PATENT DOCUMENTS 2747662  6/1978  Fed. Rep. of Germany .
2752725  6/1978  Fed. Rep. of Germany .

OTHER PUBLICATIONS

Swim et al., Science 122:466 (1955), Nonbicarbonate Buffers in Cell Culture Media.
Eagle Science 174(4008):500-3 (1971), Buffer Combinations for Mammalian Cell Cultures.
Fuenzalida, Bull W. H. O. 46:561-3 (1972), Human Pre-Exposure Rabies Immunization with Suckling Mouse Brain Vaccine.
Fuenzalida et al., Bull. W. H. O. 30:431-6 (1964), Antirabies Antibody Response in Man to Vaccine Made From Infected Suckling Mouse Brains.
W.H.O. Monograph Series No. 23, Lab. Techn. in Rabies, 3rd Ed. 367 pp. (1973): 213-200.
Fields et al., Vet. Med. Small Anim. Clin. 71(1): 37-40 Jan. 1976, Suckling Mouse Brain Rabies Vaccine: Duration of Immunity in Dogs.
Waterson, Recent Advances in Clinical Virology No. 1 Turner An Assessment of the Current Position of Rabies Vaccination in Man, pp. 79-92, (1977).
Fuenzalida et al., Instituto Bacteriol. de Chile Boletin, vol. 8:3-10 (1955), Rabies Vaccine Prepared from the Brains of Infected Suckling Mice.

Primary Examiner—Shep K. Rose
Attorney, Agent, or Firm—D. A. N. Chase

[57] ABSTRACT

A rabies vaccine composition is disclosed which comprises a sterilized suspension of proteineous suckling mice or rat brain particles of injectable particle size laden with an amount of inactivated rabies virus which is equivalent to a virus titer of from at least about $10^5$ to about $10^7$ MLD$_{50}$ per 0.01 milliliter thereof at a brain tissue concentration of from about 3 to about 6% by weight, in an aqueous buffer solution having a pH of between about 7.5 and about 8.4, and comprising an amount, dissolved therein, of between 0.03 and 0.08 moles per liter of a buffer composition comprising a mixture of an organic base of the formula $$\begin{array}{c} R_1 \\ \phantom{R}\diagdown \\ \phantom{RR}N-\underset{\underset{CH_2OH}{|}}{\overset{\overset{CH_2OH}{|}}{C}}-CH_2OH \\ \phantom{R}\diagup \\ R_2 \end{array}$$

wherein $R_1$ and $R_2$ each are hydrogen or $CH_2CH_2OH$ and an acid addition salt thereof, preferably a mixture of tris (hydroxymethyl)amino methane and its hydrochloride. The vaccine composition exhibits a high potency and its pH value remains stable over a prolonged period of time.

39 Claims, No Drawings

4,252,792

INJECTABLE RABIES VACCINE COMPOSITION AND METHOD FOR PREPARING SAME

This is a continuation of application Ser. No. 971,091, filed Dec. 19, 1978, now abandoned.

BACKGROUND OF THE INVENTION

The present invention relates to an improved rabies vaccine composition and a method for preparing same using viral-laden suckling mice or rat brain tissue.

Rabies vaccines are well known in the prior art and such vaccines are widely used in the treatment of both humans and animals. As is also well known, these vaccines, in order to be completely acceptable and fully effective, must produce or increase immunity to rabies with minimal side effects and the immunity imparted thereby must endure for a reasonably long period of time. Moreover, for these vaccines to be completely acceptable and fully effective, it is necessary that the same be a standardized preparation having a potency which remains relatively constant over reasonably long periods of time. Rabies virus can be grown in a number of tissues and tissue cultures.

In recent years, brains of suckling mice have been used as a suitable source for propagating rabies virus in the preparation of commercial animal vaccines, and the brains of suckling rats have been proposed (see, e.g., Lavender: Purified Rabies Vaccine (suckling rat brain origin) Appl. Microbiol. 19, (1970), pp. 923–927). Generally, in preparing rabies vaccines, a suspension of the viral-laden tissues in a buffered aqueous solution is prepared and then is inactivated. The pH-value of the buffered suspension and the inactivated vaccine composition is adjusted to a slightly basic value. A phosphate saline buffer solution is conventionally used for this purpose. However, several serious difficulties are encountered in conventional rabies vaccines containing a phosphate buffer:

(a) in order to maintain the desired slightly alkaline reaction and the buffering capacity of the phosphate buffer during the inactivation period, the pH-value of the suspension has to be repeatedly adjusted by adding potassium hydroxide solution;

(b) the potency of the inactivated vaccine composition relative to the amount of viral-laden tissue is adversely affected by the presence of the phosphate buffer; and (c) the pH-value of the vaccine composition is stabilized only for a limited period of time after which the pH-value slowly decreases. This change towards an acid reaction causes serious problems in that acidity is detrimental to potency and is a false indication of bacterial contamination of the vaccine. Since contamination of a vaccine with bacteria usually leads to acidification of the vaccine composition, determining the reaction of a vaccine composition with the pH indicator agent phenol red is used as a simple method for detecting bacterial contamination of vaccine compositions. After a storage period of 9 to 14 months conventional phosphate buffer containing rabies vaccine compositions often react positive to the phenol red test, even though they are not contaminated at all. Due to this false indication of bacterial contamination large amounts of vaccines are unnecessarily discarded.

SUMMARY OF THE INVENTION

It is an object of the present invention to provide a rabies vaccine composition, wherein the drawbacks of the prior art rabies vaccines are avoided.

In particular it is an object of the present invention to provide such a vaccine composition wherein the potency relative to the amount of viral laden tissue therein is increased.

It is a further object of the present invention to provide such a rabies vaccine composition which is storage-stable and wherein the pH-value is stablized within a slightly basic range for a prolonged period of time.

It is yet another object of this invention to provide such a vaccine which is a standardized preparation and which will remain potent over a relatively long period of time.

It is another object of this invention to provide such a vaccine which will produce or increase immunity to a rabies with minimal side effects. It is still another object of this invention to provide such a vaccine which, when used, will provide immunity over a relatively long period of time.

It is still another object of this invention to provide a method for preparing such vaccines, in particular a method wherein no repetitve addition of potassium hydroxide solution is needed for maintaining the pH-value of the composition during the inactivation period.

In order to accomplish the foregoing objects according to the present invention there is provided a rabies vaccine composition comprising a sterilized suspension of proteinous suckling mice or rat brain particles of injectable particle size laden with an amount of inactivated rabies virus which is equivalent to a virus titer of from at least about $10^5$ to about $10^7$ $MLD_{50}$ per 0.01 milliliter thereof at a brain tissue concentration of from about 3 to about 6% by weight, in an aqueous buffer solution having a pH of between about 7.5 and about 8.4, and comprising an amount, dissolved therein, of between 0.03 and 0.08 moles per liter of a buffer composition comprising a mixture of an organic base of the formula wherein $R_1$ and $R_2$ each are hydrogen or $CH_2CH_2OH$ and an acid addition salt thereof with an acid the anion of which is compatible with virus replication.

Preferably the inactivated rabies virus within the above defined composition is a rabies virus inactivated by $\beta$-propiolactone.

Preferably the buffer composition comprises a mixture of tris (hydroxymethyl) amino methane and its hydrochloride.

According to the present invention there is further provided a process for preparing the above defined rabies vaccine composition which comprises the steps of:

(a) suspending a sufficient amount of viral laden suckling mice or rat brain tissue material in a sterilized aqueous buffer solution having a pH of between about 7.5 and about 8.4, and comprising an amount, dissolved therein, of between 0.03 and 0.08 moles per liter of buffer composition comprising a mixture of an organic base of the formula $$\begin{array}{c} R_1 \\ \phantom{R_1}\diagdown \\ \phantom{R_1}\phantom{\diagdown}N-C-CH_2OH \\ \phantom{R_1}\diagup \phantom{N-}| \\ R_2 \phantom{\diagup} \phantom{N-}CH_2OH \end{array} \begin{array}{c} CH_2OH \\ | \\ \phantom{N-C-}CH_2OH \end{array}$$

wherein $R_1$ and $R_2$ each are hydrogen or $CH_2CH_2OH$ and an acid addition salt thereof with an acid the anion of which is compatible with virus replication, as to obtain a concentrated suspension comprising suspended therein an amount of at least about 20% by weight of proteineous viral laden suckling mice or rat brain tissue material;

(b) comminuting the suspended viral laden suckling mice or rat brain material within the concentrated suspension into particles of injectable particle size;

(c) diluting the concentrated suspension with a sufficient amount of said sterilized aqueous buffer solution to obtain a dilute suspension wherein the concentration of the proteineous viral laden brain particles is no greater than about 10% by weight;

(d) inactivating the dilute suspension preferably by means of β-propiolactone; and (e) adjusting the concentration of viral laden brain particles in the inactivated suspension to obtain the vaccine composition.

Further objects, features and advantages of the present invention will become apparent from the detailed description of the invention and its preferred embodiments which follows.

DETAILED DESCRIPTION OF THE INVENTION AND ITS PREFERRED EMBODIMENTS

The rabies vaccine composition according to the present invention is prepared and used in form of a sterilized suspension of proteineous suckling mice or rat brain particles of injectable particle size laden with the inactivated rabies virus in the aqueous buffer solution having a slightly basic pH-value. In this regard, it should be noted that the proteineous viral laden material will generally, be suspended in the aqueous buffer solution such that the same will provide the virus in the final product in a concentration sufficient to provide the desired antigenic response.

The aqueous buffer solution which is used within the vaccine composition according to the present invention contains a buffer composition comprising a mixture of an organic base of the formula:

$$\begin{array}{c} R_1 \\ \phantom{R_1}\diagdown \\ \phantom{R_1}\phantom{\diagdown}N-C-CH_2OH \\ \phantom{R_1}\diagup \phantom{N-}| \\ R_2 \phantom{\diagup} \phantom{N-}CH_2OH \end{array} \begin{array}{c} CH_2OH \\ | \\ \phantom{N-C-}CH_2OH \end{array}$$

wherein $R_1$ and $R_2$ each are hydrogen or $CH_2CH_2OH$ and an acid addition salt thereof with an acid the anion of which is compatible with virus replication.

Among the above bases tris (hydroxymethyl) aminomethane is preferred. However, N-(2-hydroxyethyl) amino tris (hydroxymethyl) methane and N,N-bis (2-hydroxyethyl) amino tris (hydroxymethyl) methane can also be used.

Any organic or inorganic acids which are not detrimental to virus replication are suitable within the acid addition salts. Hydrochlorides are preferred. Other suitable acid salts include salts of inorganic acids such as carbonates, nitrates, and salts of organic acids such as acetates, benzoates, maleates, oxalates, and succinates.

Most preferred is a mixture of Tris (hydroxymethyl) aminomethane (which in the following will be abbreviated as Tris) and its hydrochloride (which in the following will be abbreviated as Tris-HCl). The ratio between the free base and its salts within the above buffer composition of course will vary depending on the desired pH-value in the vaccine composition and the particular buffer substances which are used. For example, in order to achieve a pH-value of between 7.5 and 8.4 at a temperature of about 25° C., a by weight ratio of Tris/Tris-HCl of between about 1.18/6.35 and about 4.03/2.64 is suitable. Both Tris and Tris-HCl are commercially available from the Sigma Chemical Company, St. Louis, Mo. U.S.A., and are identified by the trademark "Trizma."

Preferably the vaccine composition is buffered to a pH-value of between about 7.8 to 8.0, and most preferably to a pH-value of about 7.8 at a temperature of about 25° C. Accordingly, the buffer solution most preferable is an about 0.05 M Tris/Tris HCl buffer solution containing about 5.32 g/l of Tris-HCl and about 1.97 g/l of Tris and having a pH-value of about 7.8 at a temperature of 25° C.

The buffer solution can be prepared by dissolving appropriate amounts of the base and its salt, e.g., of Tris and of Tris-HCl, in deionized water, or by dissolving an appropriate amount of the base, e.g., Tris, in deionized water and forming the salt in situ, by adding such an amount of the respective acid, e.g., a hydrochloric acid solution, to the solution that the pH of the initially basic solution is adjusted to the desired value. Equally the pH of an initially acidic solution can be adjusted to the desired pH-value by addition of a solution of the base.

An indicator dye such as phenol red may be added, when desired, to facilitate the adjustment of the pH and to monitor the pH during storage. Generally, when phenol red is employed the same will be added in a concentration ranging between about 1 and about 2% and the same will, generally, be used as a 1% solution thereof. Following the pH adjustment, the solution will be sterilized in accordance with methods known in prior art. For example, the same may be sterilized by heating to a temperature between 120° and 121° C. for a period of time between about 30 and 60 minutes.

When desired, preservatives, e.g., antibiotics such as penicillin, streptomycin and amphotericin B, may be added to the buffer solution or to the suspension of proteineous viral laden particles when the same is prepared.

The viral laden brain tissue from suckling mice or rats is mixed with a sufficient amount of the buffer solution to form a concentrated suspension, preferably containing between about 30 and about 60 wt% of the virus laden brain tissue. Suitably, the buffer solution will contain the buffer composition and all antibiotics required to make a final vaccine concentration between about 10 and 30 units of penicillin, 10 and 30 mcg of streptomycin sulfate and between about 5 and 10 mcg of amphotericin B per milliliter of final vaccine product. The suspension will then be subjected to high shear agitation so as to reduce the size of the brain particles to a size suitable for injection. Suitably, the high shear agitation will be continued until the particle size of all particles is within the range of about 1 to about 10 microns.

The resulting suspension may be stored at a temperature between about −40° and about −60° C. All tests required to insure the virus containing suspension of satisfactory quality will be completed prior to use of the stored virus containing suspension. Generally, this suspension comprising living, fully virulent virus will be tested for purity, safety, and potency. When the suspension is to be used in the preparation of a vaccine product, it is essential that the suspension exhibit satisfactory purity and safety and that the same have a virus titer of at least $10^5 MLD_{50}$ per 0.01 ml at a concentration of 3 wt% (for a one-year vaccine), and at least $10^7 MLD_{50}$ per 0.01 ml at a concentration of 6 wt% (for a three-year vaccine).

As has been noted, supra, the brain tissue material which is laden with the living, fully virulent viruses to be used in the vaccines of this invention will, generally, be stored in a frozen state and it will be necessary to thaw the same prior to preparation of the vaccine. When the virus laden brain tissue material to be used in the vaccine is frozen, the same will generally be rapidly thawed and then diluted with the buffer solution to a concentration ranging between about 2 and about 10 wt%.

After the suspension of viral laden brain tissue particles has been diluted, the same may then be filtered to remove particles having a size ter than 10 microns or the same may be first treated so as to inactivate the virus contained therein and subsequently be filtered.

After the viral laden brain particles have been suitably suspended in the buffer solution, and the pH thereof adjusted, the same may be inactivated, directly, or the same may be first formulated into a vaccine and the viruses inactivated at this point. In either case, any of the techniques known in the prior art to be useful for this purpose may be employed. For example, chemical inactivation may be accomplished with compounds such as β-propiolactone, or formalin or other suitable aldehydes, or the virus may be inactivated with ultraviolet light. Beta propiolactone inactivation is, however, preferred since this method results in minimal antigenic distortion.

When Beta propiolactone is used to inactivate the virus, an aqueous solution containing between about 5 and about 15 volume percent of unhydrolyzed B-propiolactone will be prepared by dissolving a pharmaceutical grade of unhydrolyzed Beta propiolactone in either distilled or deionized water. Generally, the solution containing the unhydrolyzed β-propiolactone will be prepared at a temperature between about 4° and 5° C. and the same will be added to the diluted suspension at or near this temperature such that the composite product contains β-propiolactone in a dilution within the range of about 1:1,000 and 1:10,000. The composite product will then be allowed to warm to room temperature and be subjected to periodic agitation for a period of time of between about 24 to 30 hours. During this time, the β-propiolactone will be hydrolyzed and upon complete hydrolysis, the virus will be inactivated. Either before or after inactivation of the virus a conventional suspension stabilizing agent may be added and if necessary the pH-value may be readjusted to a range of between about 7.8 and 8.0. The vaccine thus prepared will have a storage life of at least 24 months at a temperature between about 4° and 5° C. It will, of course, be appreciated that the vaccine should be stored under sterile conditions. It will also be appreciated that the vaccine may be stored in single or multiple dose containers and that the same will be used in accordance with the techniques well known in the art. Generally, a single dose will range between about 1 and 5 ml.

At this point, it should be noted that the suckling mouse or rat brain tissue cannot effectively be separated from the living, fully virulent rabies virus propagated therein without reducing the virus titer of the resulting viral suspension to an unsatisfactory level. For this reason, the brain tissue should be retained in the vaccine of the present invention. In this regard, it should be noted that a series of tests completed on test animals with the vaccine of this invention indicate that there is no reaction whatever to the presence of this tissue in the vaccine. It should also be noted that the rabies vaccine compositions prepared in accordance with the present invention exhibit a potency, as determined in mice, of at least ten times the NIH minimum standard. While applicant does not wish to be bound by any particular theory, it is believed that this increased potency is the result of the relatively high virus titers obtained when the virus is supplied with a high antigenic mass source such as the viral laden suckling mice or rat brain tissue and the vaccine composition is buffered by means of the buffer composition heretofore described. In this regard, it should be noted that these relatively high potencies will be consistently obtained when care is exercised to insure the high titers heretofore described and to insure that the final vaccine contains at least about 2 wt% of the viral laden brain tissue.

In the following a method of obtaining the viral laden suckling mice or rat brain tissue which is used as a starting material for the presently claimed rabies vaccine composition will be described:

Preparation of viral laden brain tissue starting material

It has been found that a high antigenic mass rabies virus can be propagated in suckling mouse brain or rat brain tissue and that standardized vaccine preparations can be prepared with rabies virus propagated in this manner.

Generally, vaccine production quantities of a high antigenic mass rabies virus can be propagated in suckling mouse or rat brain tissue starting with any of the strains of rabies virus generally available for this purpose. In this regard, the CVS strain of rabies virus has been found particularly effective for use in the propagation of such a high antigenic mass virus. Such viruses are, of course, available from the National Institute of Health, Bethesda, Md. as well as from other Culture Depositories throughout the country and the same may be obtained as a lyophilized suspension.

The high antigenic mass rabies virus can be propagated starting from a lyophilized suspension of a suitable rabies virus obtained from one of the Culture Depositories. Generally, the lyophilized suspension, when reconstituted, will have a virus titer between about $10^6$ and $10^7 MLD_{50}$ per 0.03 ml. This suspension will then be intracerebrally inoculated into several suckling mice or rats. The actual size of the dose is not, of course, critical so long as each of the mice or rats receive a dose sufficient to induce rabies in the inoculated species. Suitably, suckling mice will be injected with a dose having a virus titer between about 100 and 150 $MLD_{50}$.

As will be readily apparent, the intracerebral inoculation of the live rabies virus will produce typical rabies symptoms in the mice or rats and permit the rabies virus to propagate through the brain cell tissues. Generally, the virus will be permitted to incubate for a period between about 4 and 5 days and the virus may be harvested after this period. As will be pointed out more fully, hereinafter, uninoculated control litters from the same source of mice or rats will be observed during and after the incubation period to insure that the animals used for propagation did not suffer from abnormal symptoms.

After the necessary tests have been completed to insure that the inoculated animals did not suffer from other diseases, the propagated rabies virus will be harvested by removing the brain of the inoculated suckling animals. This can, of course, be accomplished by any suitable technique known in the art. For example, inoculated suckling mice will be held at a temperature of between about −40° and −60° C. after the virus incubation period and prior to harvesting. The frozen mice will, then, be thawed just prior to harvest and the rabies virus laden brain tissue removed, generally, at or near room temperature. Following the harvest, the rabies virus laden brain will be suspended in a suitable medium and stored at a temperature between about −40° and −60° C. A portion of the brain tissue suspension will, generally, of course, be withdrawn and tested before the remaining portion thereof is used for any purpose.

Generally, the first batch of harvested viral laden brain tissue will be used as a master seed for all future production of living, fully virulent viruses for use in the vaccine of this invention. When this is done, the first batch will be extensively tested to insure that the same is completely satisfactory for its intended purpose. As will be readily apparent, when the first batch of harvested brain is used exclusively to inoculate suckling animals for the purpose of propagating the virus for subsequent vaccine production, a relatively large source of seed virus will be provided and each batch of vaccine produced therewith will be more uniform since each will be started with the virus from the same source. This results in a more uniform vaccine product and this method of subsequent propagation is preferred for this reason. Notwithstanding this, however, a continuing supply of living, fully virulent virus could be provided by using a portion of each batch of viral laden brain tissue to inoculate additional suckling mice or rats with the remaining portion used to produce a vaccine in accordance with this invention. As will be readily apparent, however, propagation in this manner would be unfeasible for industrial vaccine production due to the extensive tests that must be completed on each batch of seed virus to insure the high quality product of this invention.

When the first batch of harvested viral laden brain tissue is used as a master seed, the same will, generally, be suspended in a suitable media at a concentration of about 20% fetal bovine serum and the suspension will contain about 1000 units penecillin, 1000 mcg streptomycin sulfate and 10 mcg amphotericin B per milliliter thereof. The particular concentration of fetal bovine in suspension is not, of course, critical and the particular concentration employed can be varied. Moreover, the concentration of antibiotics in the suspension is also not critical. Such antibiotic addition will, however, be accomplished, generally, in accordance with Federal Regulation 9 CFR 114.10D. It is, however, essential that the master seed have a virus titer of at least $10^{7.2}$ $MLD_{50}$ per 0.01 ml at a 20% concentration to insure the high potency of the present invention.

Generally, when the first batch of harvested viral laden brain tissue is to be used as a master seed, the same will be subjected to high shear agitation so as to reduce the particle size of the suspended brain tissue to between about 1 and 10 microns. This can, of course, be most easily accomplished by subjecting the suspension to high shear agitation at a relatively high concentration of at least about 20 wt% and thereafter diluting the same to the desired concentration for storage. Moreover the master seed will, generally, be stored, thawed and used, as required, for subsequent testing and/or the production of working seed.

After a first batch of viral laden brain tissue has been prepared, all subsequent batches of brain tissue containing the living, fully virulent rabies virus will be produced by inoculating suckling mice or rats with viral laden brain tissue. Generally, this will be accomplished, exclusively, with the first batch of viral laden brain tissue which will be preserved as a master seed. As has been noted, supra, however, this can be accomplished by using a portion of the first or any subsequent batch of viral laden brain tissue therefor. In either case, the viral laden brain tissue will be suspended in a suitable diluent and diluted such that each inoculated suckling animal receives a dose which is sufficient for inducing rabies. Suitably a suckling mouse receives a dose having a strength of between about 100 and 500 $MLD_{50}$. Generally, this will be achieved with a dose of about 0.01 ml, although other size doses could be used.

Broadly, any number of mice or rats could be inoculated and the viral laden brains thereof subsequently pooled to produce a vaccine in accordance with this invention. Generally, however, the number of inoculated animals will range between about 1,000 and 10,000 and about 50,000 and 500,000 doses of a vaccine product will be produced from each such batch. After the inoculation of each batch of suckling animals, the animals will be observed for typical rabies symptoms and the viral laden brain tissue harvested after the animals become moribund. In this regard, it should again be noted that the moribund animals can be stored at a temperature between about −40° and about −60° C. for a period of time of about two weeks. The moribund animal will, generally, then be stored and all tests necessary to insure that healthy animals were inoculated will be completed before the viral laden brain tissue is harvested. When these tests are completed, the brains will be harvested in the same manner as indicated previously with respect to the first batch prepared and then suspended in a suitable medium. Following this suspension, the viral laden suspension will also be tested so as to insure that the same is suitable for the preparation of a vaccine within the scope of this invention.

When the rabies virus is to be harvested directly after the animals have become moribund, this can be accomplished directly by extraction of the brain. When the virus is to be harvested from stored animals, however, it will be necessary to thaw the frozen, moribund animals prior to removing the brain. This will, generally, be accomplished by immersing the frozen animal in a water bath at a temperature between 5° and 15° C. The viral laden brains will then be removed at or near room temperature. Though this is not necessarily required, the skin surface of the animals may be treated with tincture of iodine prior to extraction of the brain and the extrusion may be accomplished with a suitably sized hypodermic needle inserted tangentially in the forward aspect of the cranial cavity. Generally, the hypodermic needle will be attached to a safety-trapped vacuum system. Generally, the extracted brains will be cooled to a temperature between about −50° and +5° C. immediately after removal thereof.

After the brains have been removed from the inoculated suckling mice or rats the obtained virus laden brain tissue material can be frozen or can directly be used within the process according to the present invention. For example, it may be directly diluted with the buffer solution to form the above mentioned concentrated suspension which again can be frozen and for a period of time be stored in frozen form, for example until all tests which are required have been performed as samples of suspension.

At this point, it should be noted that the various tests performed on both the primary seed and subsequent batches of viral laden brain tissue form no part of the present invention and all may be completed in accordance with techniques well known in the prior art. Nonetheless, it should be noted that the batch used as the primary master seed would normally be tested for purity, safety, potency, sterility, and identity while subsequent batches of viral laden brain tissue would be tested only for purity, safety, and potency. In this regard, it can be noted that both the purity and sterility tests may be accomplished in accordance with procedures set forth in Title 9 of the Federal Regulations. Safety, on the other hand, may be determined by intracerebrally inoculating any of several animal species with the inactivated virus and observing the inoculated species for a period of about 21 days. Identity, on the other hand, may be determined by inoculating guinea pigs and or mice intracerebrally and observing the development of typical rabies symptoms; in cell cultures by fluorescent antibody microscopy, using specific fluorescein labeled rabies antiserum; and by the virus' ability, when inactivated, to protect guinea pigs and/or mice against lethal challenge of rabies virus. Finally, potency may be determined by inoculating any of several animal species, in accordance with known procedures, with a vaccine containing the inactivated virus and determining the minimum concentration or dose required to protect the species thus inoculated.

In general, any strain of mice or rats may be used to propagate the rabies virus which is most useful in the present invention. Care should be exercised, however, to remove any animals evidencing disease symptoms from the colony. Any such animals thus removed should then be autopsied and examined grossly and microscopically for specific disease lesions so as to insure that the animals actually used for the propagation of the rabies vaccine are suitable therefor. In addition, representative litters of suckling animals should be routinely examined for LCM virus. Moreover, the pooled brain suspensions should be routinely tested for murine leukemia particles and serologic endpoint titrations should be run on individual samples to determine murine virus antibodies for the following: reovirus type 3 (HI), pneumonia virus of mice (PVM) (HI), K virus (HI), Theiler's encephalomyelitis (GDVII) (HI), polyoma (HI), Sendai (HI), minute virus of mice (MVM) (HI), mouse advenovirus (CF), mouse hepatitis virus (CF), lymphocytic choriomeningitis virus (LCM) (CF) and ectromelia (vaccine virus HI test). In addition, routine cultures should be obtained from the vital organs of several production females for the purpose of determining the absence of bacterial pathogena. Generally, all of these tests will be completed in accordance with procedures well known in the prior art and all will be completed on the suckling mice or rats used to prepare the master seed and the same will be routinely accomplished thereafter.

Notwithstanding the fact that essentially any strain of mice or rats could be used to propagate the rabies virus useful in the vaccines of this invention, it is preferred that a strain known to be useful for medical purposes be used and most preferred that a germ-free strain be employed for propagation of the virus. In this regard it should be noted that a germ-free colony of suitable mice has been developed and the same is designated as Strain ICR-MCR by the supplier, Mid-Continental Research Animals, Inc. of Shawnee, Kansas.

In the following the preparation of a rabies vaccine composition comprising a sterilized suspension of viral laden proteineous suckling mice brain particles according to a preferred embodiment of the invention will be described:

Preferred embodiment (a) Preparation of starting viral laden suckling mice brain tissue material.

The rabies virus for vaccine production is propagated by injecting suckling mice intracerebrally at an age between two and five days with a working seed containing living, fully virulent rabies virus, which working seed is prepared by diluting a master seed to a virus titer between about 100 to 500 $MLD_{50}$ per dose. The master seed, in turn, is prepared by inoculating 2-5 day old suckling mice from the same source as that used for future propagation with a CVS strain rabies virus and then harvesting the viral laden brain tissue. The master seed has a virus titer* of at least $10^{7.2}$ $MLD_{50}$ per 0.01 ml at a concentration of 20 wt%. The production virus is then harvested from the inoculated mice after the development of typical rabies symptoms, when the mice have become moribund (4-5 days) and when 2-5% of the inoculated mice have died. The thus propagated virus will be harvested and used only if there is no evidence of atypical rabies virus propagation and only if the results of all tests noted, heretofore, as well as any others that might be required by Federal Regulations such as those required by Title 9 of the code of Federal Regulations, are satisfactory.

*In the definition of the virus titer $10^{7.2}$ indicates the number of virus particles at the specified quantity and concentration of the mice brain suspension. $MLD_{50}$ refers to the dilution at which death loss of 50% of the mice occurs.

Until it is determined that the virus are satisfactory for harvest, the virus laden mice are stored in plastic containers at a temperature between about −45° and −55° C. After satisfactory results have been obtained and the mice are ready for harvest, the mice are thawed by immersing the same in water (in the plastic containers) at a temperature between about 5° and 15° C. Once the mice have been thawed, the skin surface thereof is treated with tincture of iodine and the brains withdrawn from the cranial cavity using a 15 gauge hypodermic needle inserted tangentially in the forward aspect of the cranial cavity in combination with a vacuum aspirator. After the brains have been harvested, the same are pooled together.

(b) Preparation of rabies vaccine.

The pooled viral laden brain material is subsequently suspended in a 0.05 M solution of Tris-HCl/Tris buffer containing a sufficient amount of antibiotics to provide 10 to 30 units of penicillin, 10 to 30 mcg atreptomycin sulfate and 5 to 10 mcg amphotericin B per milliliter of final vaccine product. In the preferred embodiment, the viral laden mouse brains will be suspended, initially, at a concentration of 30 to 60 wt% and then subjected to high shear agitation so as to reduce the particle size of the suspended mouse brains to between about 1 and 10 microns.

Between about 2 and 10 ml of the suspension thus prepared are withdrawn and diluted for purposes of further tests. The remaining portion is stored at a temperature between about $-45°$ and $-55°$ C. and subsequently used (after satisfactory test results have been obtained) in the preparation of a rabies vaccine.

In the preparation of the rabies vaccine, the concentrated (30–60 wt%) frozen suspension is thawed at a temperature of between 4° and 5° C. and diluted to a concentration of about 2.5 to about 6 wt%. Dilution is effected with an aqueous 0.05 M solution of Tris/Tris-HCl buffer and may further contain any additional antibiotics which might be required to provide the desired antibiotics concentration in the final product. The diluted suspension then is filtered under sterile conditions to remove particles greater than 10 microns. The pH value of the resulting suspension is between about 7.5 and 8.4.

During the dilution, filtration and adjustment of the pH, the suspension is maintained at a temperature of between 0° and 5° C. Following the dilution, filtration and pH adjustment, the rabies virus then is inactivated with unhydrolized $\beta$-propiolactone. As has been noted, supra, this can be accomplished with a solution containing between about 5 and 15 wt% of unhydrolized $\beta$-propiolactone such as Purified Fellows (Medical) Beta pripiolactone. The $\beta$-propiolactone solution is suitably added to the diluted suspension with both at a temperature of between about 4° and 5° C. Thereafter the combined mixture will be allowed to become fully hydrolized. Generally, this will be accomplished at room temperature within about 24 to about 30 hours. The suspension should be agitated periodically throughout the hydrolyzation period.

To insure standardization of the product, the concentration of suspended tissue in the product must be between about 2.5 and 6 wt%. The resulting product may be packaged or stored under sterile conditions.

The following Examples will further clarify the present invention and demonstrate the effectiveness thereof. The same are not, however, intended to limit the invention in any way.

EXAMPLE 1

(A) Preparation of viral laden suckling mice brain tissue starting material for a master seed suspension For preparing a concentrated suspension of living, fully virulent rabies virus three 1.0 ml ampules of a 10 wt% lyophilized mouse brain suspension were obtained from the Division of Biologic Standards, National Institute of Health, Bethesda, Maryland, containing the CVS rabies virus strain. The ampules were identified by Serial No. CVS-31. The three ampules were then pooled, reconstituted and diluted with an aqueous 0.05 M Tris/Tris HCl buffer solution and the diluted suspension was used to intracerebrally inoculate 132, three day old, suckling mice. The inoculation was accomplished with a calibrated, automatic syringe inserted approximately midway into the cranial cavity at an adequate depth into one of the cerebral hemispheres and each of the inoculated mice received 0.01 ml of the viral suspension. The inoculated mice developed typical rabies symptoms after three days and become moribund in about four days. The moribund, inoculated mice were then stored at a temperature of $-50°$ C. for about two days. Following this period of storage, the virus laden brain tissue was separated from the inoculated mice by first warming the frozen mice to a tempeature of 5° C., treating the skin surface of the inoculated mice with a 2% tincture of iodine and then withdrawing the brain by inserting a 15 gauge hypodermic needle tangentially in the forward aspect of the cranial cavity. The hypodermic needle was attached to a safety-trapped vacuum system which was closed between the harvest of each individual mouse brain. Twenty-five grams of brain tissue were withdrawn from 120 of the 132 inoculated mice.

The stock breeders used to produce the mice which were inoculated in this and subsequent Examples were from the germ-free strain designated ICR-MCR and available from Mid-Continent Research Animals, Inc., Shawnee, Kansas. These breeders were housed in sterile facilities and used solely for the purpose of producing a gnotobiotic colony of mice to be used to propagate the rabies virus useful in the vaccines of this invention. In this regard, it should be noted that this was accomplished by retaining a portion of the progeny of the first and subsequent generations for future breeding of suckling mouse breeders and using the remaining portion of the first and subsequent generations directly for breeding of suckling mice to be used in the propagation of the rabies virus.

(B) Preparation of a sterilized buffer solution:

A buffer solution was prepared by mixing 5.32 g/l Tris HCl and 1.97 g/l Tris base in 1000 ml deionized water and 2 ml of a 1% solution of phenol red. The pH of the solution is then at a value of 7.8. The solution was then sterilized by autoclaving at 121° C. for 30 minutes and tested for sterility. The suspension medium was found satisfactory for use in the preparation of vaccines and was stored under sterile conditions.

(C) Preparation of a concentrated primary master seed suspension of viral laden suckling mice brain tissue:

The tissue, which was obtained as described above in step A was suspended in 100 ml of a sterilized, aqueous 0.05 M solution of Tris-HCl/Tris buffer which contained a sufficient amount of antibiotics to provide 1,000 units of penicillin per liter, 1,000 mcg per liter of streptomycin sulfate and 10 mcg amphotericin B per milliliter of suspension. The resulting suspension contained 20 wt% of the virus laden brain tissue and the same was subjected to high shear agitation for a period of six minutes so as to reduce the size of the brain particles to a size between about 1 and 10 microns. Twenty-five milliliters of the 20 wt% suspension was then removed for testing and the remainder of the 20 wt% solution was then dispensed in 0.5 ml amounts in 200 ampules and stored at 31 50° C.

The concentrated viral suspension prepared by the method of Step C this Example was tested for purity, safety, potency, sterility and identity. The virus titer of the suspension was found to be $10^{7.2}$ $MLD_{50}$ per 0.01 ml thereof and the suspension was found to be satisfactory for use as a primary master seed.

(D) Preparation of a diluted secondary master seed suspension of viral laden suckling mice brain tissue:

A secondary master seed was prepared by diluting 0.4 ml of the primary master seed suspension prepared in Step C with 399.6 ml of a sterilized 0.05 M aqueous solution of Tris-HCl/Tris buffer. A portion of the secondary master seed was tested for sterility and the remainder dispensed in 3 ml ampules and stored at $-50°$ C. The secondary master seed of this Example was found to be satisfactory for use in the preparation of additional rabies virus.

(E) Preparation viral laden suckling mice brain tissue starting material for a vaccine composition:

3 ml of the secondary master seed obtained in Step D were thawed and diluted with a sterilized 0.05 M aqueous solution of Tris-HCl/Tris buffer prepared in the manner described in Step B so as to provide a suspension of living, fully virulent rabies virus having a virus titer between 100 and 500 $MLD_{50}$ per 0.01 ml thereof. 0.01 ml of this suspension was then injected intracerebrally into each of 92, two to four day old, suckling mice produced with the breeders described in Step A. Following these inoculations, the suckling mice were returned to their cages to incubate the virus. After about three days, the inoculated mice developed typical rabies symptoms and all of the inoculated mice became moribund after 4–5 days. The moribund mice were then stored at −50° C. until tests on uninoculated litters of mice from the same source were completed.

After these tests were completed and satisfactory results obtained, 75 of the stored, moribund mice were then thawed and the living, fully virulent rabies viruses harvested by removal of the brain tissue from the mice in the same manner as that set forth in Step A. After separation, the brains from these 75 inoculated mice were pooled to yield 15 grams of brain tissue.

(F) Preparation of concentrated suspension of viral laden suckling mice brain tissue for producing vaccine compositions:

The viral laden brain tissue obtained in Step E was then suspended in a sterilized, 0.05 M solution of Tris-HCl/Tris buffer further containing, for example, 600 units of penicillin, 600 mcg streptomycin sulfate and 50 mcg amphotericin B per ml thereof. Two different suspensions were prepared containing respectively 30 and 60% by weight of the viral laden mice brain tissue in the buffer solution. The 30% suspension is suitable for preparing a vaccine composition providing a one-year immunization period; and the 60% suspension is suitable for preparing a vaccine composition providing a three-year immunization period.

The 30 and 60 wt% suspensions were subjected to high shear agitation in a homogenizer at a temperature of about 5° C. so as to reduce the size of the brain tissue to a value of between about 1 and 10 microns. Two milliliters of each suspension was then removed for testing and the remainder stored at −50° C. The suspensions were tested for potency, mycoplasma and sterility. As a result of these tests, the 60 wt% suspension was found to have a virus titer of $10^{7.38}$ $MLD_{50}$ per 0.01 ml at a concentration of 6 wt% and to be satisfactory for use in the preparation of a three-year rabies vaccine. The 30 wt% suspension was found to have a virus titer of $10^{5.37}$ $MLD_{50}$ per 0.01 ml at a concentration of 3 wt%, satisfactory for a one-year vaccine.

(G) Preparation of inactivated rabies vaccine compositions:

After satisfactory results were obtained in the quality control tests, the concentrated 30 and 60 wt% viral laden mouse brain suspensions obtained in Step F were thawed by warming to a temperature of 4°–5° C. and then diluted to form 3 and 6 wt% suspensions respectively by adding 9 ml of the buffer solution prepared in Step B to one ml of the concentrated suspension so as to produce 375 ml each. The diluted suspensions which are maintained at about 4°–5° C. throughout were then filtered through a sterile Millipore clarifying screen to remove particles having a particle size greater than 10 microns. Subsequently 25 ml of each of the suspensions were withdrawn for subsequent testing. The living, fully virulent viruses contained in the remaining portion of each dilute suspension were inactivated with β propiolactone. The deactivation was accomplished with a solution containing 10 wt% of β propiolactone. The β propiolactone solution was prepared by adding a medicinal grade of unhydrolyzed B propiolactone (Fellows-Medical) at a temperature of −20° C. to deionized water at a temperature of 5° C. After the β propiolactone was added to the water, the mixture was agitated, briefly, to insure the formation of a solution and the same was then used directly in the inactivation of the rabies virus in the diluted suspensions. In this regard, it should be noted that best results are obtained when the β propiolactone solution is added to the diluted suspension within five minutes after preparation thereof. The β propiolactone solution was transferred to the diluted suspension with sterile filtered air pressure at a rate of 4.0 ml per liter of diluted suspension in an amount providing a 1:2500 dilution of β propiolactone in the combined product. The suspension was then allowed to warm to room temperature and the same was agitated periodically for a period of 24 hours.

In order to insure a standardized product, it is essential that the final vaccine product contain at least 2.5 wt% of the viral laden mouse brain tissue extracted from the suckling mice and used in the preparation of the vaccine for a one-year immunization period and 5 wt% for a three-year immunization period in dogs and cats.

Each of the one and three year vaccines prepared in this Example yielded 310 ml. The vaccine compositions were packaged in a plurality of single and 10 dose vials. The packaging was, of course, accomplished in sterile conditions and the containers employed were of the conventional borosilicate type. Each of the single dose bottles contained 1.3 ml of the vaccine and the 10 dose bottles contained 11.4 ml each.

EXAMPLE 2

The vaccine compositions obtained in Example 1 were tested for inactivation by inoculating 0.03 ml intracerebrally into mice 21 days old. In one series of tests, 10 mice were injected with the vaccine composition as prepared. In the second series, 10 mice were injected with a 1:10 dilution of the vaccine composition and in a third series of tests, 10 mice were injected with the composition dilution of 1:100. The mice in all three series survived during the entire 21 day observation period thus indicating that the rabies virus in the vaccine had been inactivated.

EXAMPLE 3

The relative potency or antigenic factor of the vaccine prepared in Step G of Example 1 was determined in accordance with the procedure set forth for the Modified National Institute of Health potency test, which procedure is summarized in the World Health Organization "Laboratory Techniques in Rabies" 2nd Edition, 1966. The materials and methods used, and results obtained are as follows:

Six 100 ml test samples of a concentrated suspension containing 60% of viral laden mice brain particles each were diluted tenfold to obtain a 6% suspension.

Three of the test samples were diluted with a buffer solution according to the present invention which had been prepared by mixing 5.32 g/l of the Tris HCl with 1.97 g/l of the Tris base and 7.2 g/l NaCl. Phenol red was added to the solutions at a concentration of 3 mls/l of a 1% solution.

The remaining three test samples were diluted with a conventional phosphate buffered saline solution comprising 0.01 M dibasic potassium phosphate and NaCl (7 g/l).

The six resulting dilute test suspensions were inactivated with Beta propiolactone at a concentration of 1:2500 for a 24-hour period carried out at a room temperature (22°-23° C.).

The pH of the six dilute 6% mouse brain test suspensions was maintained at a pH-value of 7.8 during the inactivation period, by using 1 N KOH if necessary. Table No. 1 below gives the amount of 1 N KOH which was needed to maintain the pH of the test suspensions at 7.8.

At the end of the 24-hour inactivation period, samples from each of the six test suspensions were aseptically drawn with a volumetric pipet and tested for the presence of live virus using the mouse safety test. Dilutions of $10^0$, $10^{-1}$, and $10^{-2}$ were inoculated into 10 mice for each dilution of the six test suspensions and observed for 21 days. No rabies deaths attributable to live virus were observed.

An amount of 20% v/v stabilizer was added to each of the 6% mouse brain test suspensions to obtain six test-vaccine compositions. The stabilizer employed was pharmaceutical grade Carbopol supplied by B. F. Goodrich, and was added at a weight/volume concentration of 3 g/l to provide a final stabilizer content of 0.5 g/l in the vaccine compositions.

Vaccine compositions 1-3 contained the Tris/Tris HCl buffer solution and vaccine compositions 4-6 contained the phosphate buffer solution.

The completed test vaccine compositions were throughly mixed by agitation for 2 hours after the addition of the stabilizer.

Samples of the completed test vaccine compositions were taken for safety and potency testing.

Vaccines No. 1 through 6 were tested for potency using the NIH potency test after completion of the final product to determine the antigenic value of the six experimental lots.

Vaccines 1 and 4 were incubated at 37° C. for 230 hours and the potency of each lot tested.

Vaccines 2 and 5 were incubated 54 days at room temperature (22°-23° C.) and the potency of each lot tested.

Vaccines 3 and 6 were held in the cooler at 5° C. for 59 days and the potency of each lot tested.

The antigenic values obtained from the NIH potency after incubation for all samples are listed in Table 2 below.

TABLE NO. 1

Addition of 1NKOH during the 24 hour Inactivation Period

| Tris buffered suspensions | | Phosphate buffered suspension | |
|---|---|---|---|
| Suspension No. | 1NKOH Added (mls) | Suspension No. | 1NKOH Added (mls) |
| 1 | 0 | 4 | 16 |
| 2 | 0 | 5 | 14 |
| 3 | 0 | 6 | 20 | rabies virus.

TABLE NO. 2

Antigenic Values of Rabies Vaccine Formulated Tris/Tris-HCl Buffered Saline and Phosphate Buffered Saline
The potencies of the six vaccines were tested by the NIH Potency test after incubation for 230 hours at 37° C., 54 days at room temperature and 59 days at 5° C.

Antigenic Values of the Vaccines Before and After Incubation at 37° C. for 230 hours.

| Antigenic Value Before Incubation Vaccine No. 1 | | Antigenic Value After Incubation Vaccine No. 1 | |
|---|---|---|---|
| *EPD$_{50}$ Test Vaccine | 156.3 | EPD$_{50}$ Test Vaccine | 130.0 |
| EPD$_{50}$ Ref. Vaccine | 23.07 | EPD$_{50}$ Ref. Vaccine | 22.03 |
| Antigenic Value | 6.78 | Antigenic Value | 5.90 |
| Vaccine No. 4 | | Vaccine No. 4 | |
| EPD$_{50}$ Test Vaccine | 208.4 | EPD$_{50}$ Test Vaccine | 112.2 |
| EPD$_{50}$ Ref. Vaccine | 23.17 | EPF$_{50}$ Ref. Vaccine | 17.42 |
| Antigenic Value | 4.99 | Antigenic Value | 2.99 |

Antigenic Values of Vaccines Incubated At Room Temp (22-23° C.) for 54 Days

| AV Before Storage Vaccine No. 2 | | AV After Storage Vaccine No. 2 | |
|---|---|---|---|
| EPD$_{50}$ Test Vaccine | 146 | EPD$_{50}$ Test Vaccine | 176 |
| EPD$_{50}$ Ref. Vaccine | 31 | EPD$_{50}$ Ref. Vaccine | 27.6 |
| Antigenic Value | 7.26 | Antigenic Value | 6.4 |
| Vaccine No. 5 | | Vaccine No. 5 | |
| EPD$_{50}$ Test Vaccine | 167 | EPD$_{50}$ Test Vaccine | 218 |
| EPD$_{50}$ Ref. Vaccine | 23.3 | EPD$_{50}$ Ref. Vaccine | 37.1 |
| Antigenic Value | 4.7 | Antigenic Value | 2.7 |

Antigenic Values of Vaccine refrigerated at 5° C. for 59 Days

| Vaccine No. 3 | | Vaccine No. 3 | |
|---|---|---|---|
| EPD$_{50}$ Test Vaccine | 184.2 | EPD$_{50}$ Test Vaccine | 228 |
| EPD$_{50}$ Ref. Vaccine | 28.5 | EPD$_{50}$ Ref. Vaccine | 32.5 |
| Antigenic Value | 6.46 | Antigenic Value | 5.07 |
| Vaccine No. 6 | | Vaccine No. 6 | |
| EPD$_{50}$ Test Vaccine | 133 | EPD$_{50}$ Test Vaccine | 163 |
| EPD$_{50}$ Ref. Vaccine | 28.5 | EPD$_{50}$ Ref. Vaccine | 32.6 |
| Antigenic Value | 4.67 | Antigenic Value | 3.67 |

*EPD$_{50}$ is that dose where 50% of the mice are protected when challenged with live rabies virus.

The results from the above test suspensions confirmed that the pH of the Tris/Tris-HCl buffered suspensions did not fluctuate after the addition of β propiolactone as did the mouse brain virus suspensions buffered with the phosphate buffer. (See Table 1).

The pH of the Tris/Tris-HCl buffered suspensions was buffered at a pH of 7.8 throughout the inactivation procedures and there was lowering of pH (6.9-7.2) of the phosphate buffered lots during the same inactivation period and it was necessary to add 1 N KOH to raise the pH of the phosphate buffered experimental lots.

Results of the safety test in mice revealed no rabies deaths attributable to live virus in all groups tested.

The results of the NIH potency show that there were differences in the antigenic values of the vaccines prepared using Tris/Tris-HCl buffer and the vaccines prepared using phosphate buffer (See Table 2).

As will be readily apparent, the foregoing Examples clearly indicate that the vaccines of this invention are completely acceptable and fully effective for the purpose intended. As is also readily apparent, the rabies vaccine prepared in accordance with this invention does produce immunity in all tested animal species to this disease.

Although the present invention has been described and illustrated by reference to particular embodiments thereof, it will be readily apparent that the same lends itself to various modifications which will be obvious to those of ordinary skill in the art. Accordingly, reference should be made solely to the appended claims to determine the scope of this invention.

What is claimed:

1. A rabies vaccine composition comprising a sterilized suspension of proteineous suckling mice or rat brain particles of injectable particle size laden with an amount of inactivated rabies virus which is equivalent to a virus titer of from at least about $10^5$ to about $10^7$ $MLD_{50}$ per 0.01 milliliter thereof, at a brain tissue concentration of from about 3 to about 6% by weight, in an aqueous buffer solution having a pH of between about 7.5 and about 8.4, and comprising an amount, dissolved therein, of between 0.03 and 0.08 moles per liter of a buffer composition comprising a mixture of an organic base of the formula $$\begin{array}{c} R_1 \\ \phantom{R}\diagdown \\ \phantom{RR}N-C-CH_2OH \\ \phantom{R}\diagup \phantom{NN}| \\ R_2 \phantom{NN} CH_2OH \end{array} \begin{array}{c} CH_2OH \\ | \\ \end{array}$$

wherein $R_1$ and $R_2$ each are hydrogen or $CH_2CH_2OH$ and an acid addition salt thereof with an acid the anion of which is compatible with virus replication.

2. A rabies vaccine composition comprising a sterilized suspension of a minor concentration by weight of proteineous suckling mice or rat brain particles of injectable particle size laden with inactivated rabies virus, in an aqueous buffer solution having a slightly basic pH value and an amount, dissolved therein, of a buffer composition sufficient to stabilize the pH at said value, said buffer composition comprising a mixture of an organic base of the formula $$\begin{array}{c} R_1 \\ \phantom{R}\diagdown \\ \phantom{RR}N-C-CH_2OH \\ \phantom{R}\diagup \phantom{NN}| \\ R_2 \phantom{NN} CH_2OH \end{array} \begin{array}{c} CH_2OH \\ | \\ \end{array}$$

wherein $R_1$ and $R_2$ each are hydrogen or $CH_2CH_2OH$, and an acid addition salt thereof with an acid the anion of which is compatible with virus replication.

3. The rabies vaccine composition as defined in claim 2, wherein the aqueous buffer solution is a 0.03 M to 0.08 M solution of said buffer composition.

4. The rabies vaccine composition as defined in claim 2, wherein the buffer composition comprises a mixture of tris (hydroxymethyl) amino methane and its hydrochloride.

5. The rabies vaccine composition as defined in claim 4, wherein the aqueous buffer solution is a 0.05 M solution of said buffer composition.

6. The rabies vaccine composition as defined in claim 4, wherein in the buffer composition the by weight ratio between tris (hydroxymethyl) amino methane and its hydrochloride is from about 1.18/6.35 to 4.03/2.64.

7. The rabies vaccine composition as defined in claim 6, wherein the by weight ratio is about 1.97/5.32.

8. The rabies vaccine composition as defined in claim 2, wherein said pH value is between about 7.5 and about 8.4.

9. The rabies vaccine composition as defined in claim 2, wherein said pH value at 25° C. is between about 7.8 and about 8.0.

10. The rabies vaccine composition as defined in claim 2, wherein said brain particles are laden with an amount of said inactivated rabies virus which is equivalent to a virus titer of from at least about $10^5$ to about $10^7$ $MLD_{50}$ per 0.01 milliliter of said suspension.

11. The rabies vaccine composition as defined in claim 2, which comprises an amount of said brain particles of between about 2.5 and about 6 percent by weight.

12. The rabies vaccine composition as defined in claim 11, wherein the amount of brain particles is between about 2.5 and about 3.5 percent by weight.

13. The rabies vaccine composition as defined in claim 11, wherein the amount of brain paticles is between about 5 and about 6 percent by weight.

14. The rabies vaccine composition as defined in claim 1, wherein the inactivated rabies virus is a rabies virus deactivated by Beta propiolactone.

15. The rabies vaccine composition as defined in claim 2, which further comprises an indicator dye.

16. The rabies vaccine composition as defined in claim 15, wherein the indicator dye is phenol red.

17. The rabies vaccine composition as defined in claim 2, which further comprises a preservatively effective amount of an antibiotic.

18. The rabies vaccine composition as defined in claim 17, wherein the antibiotic is selected from the group consisting of penicillin, a streptomycin salt, amphotericin B and mixtures thereof.

19. The rabies vaccine composition as defined in claim 2, wherein the particle size of the brain particles is between about 1 and about 10 microns.

20. A process for preparing the rabies vaccine composition containing an antigenically effective concentration of proteineous viral laden brain particles as defined in claim 2, which comprises the steps of (a) suspending a sufficient amount of viral laden suckling mice or rat brain tissue material in a sterilized aqueous buffer solution having a slightly basic pH value and an amount, dissolved therein, of a buffer composition sufficient to stabilize the pH at said value, said buffer composition comprising a mixture of an organic base of the formula $$\begin{array}{c} R_1 \\ \phantom{R}\diagdown \\ \phantom{RR}N-C-CH_2OH \\ \phantom{R}\diagup \phantom{NN}| \\ R_2 \phantom{NN} CH_2OH \end{array} \begin{array}{c} CH_2OH \\ | \\ \end{array}$$

wherein $R_1$ and $R_2$ each are hydrogen or $CH_2CH_2OH$, and an acid addition salt thereof with an acid the anion of which is compatible with virus replication, to obtain a concentrated suspension having suspended therein an amount of at least about 20 percent by weight of proteineous viral laden suckling mice or rat brain tissue material;

(b) comminuting the suspended viral laden suckling mice or rat brain tissue material within the concentrated suspension into particles of injectable particle size;

(c) diluting the concentrated suspension with a sufficient amount of said sterilized aqueous buffer solution to obtain a dilute suspension having a concentration of the proteineous virual laden brain particles of no greater than about 10 percent by weight;

(d) inactivating the dilute suspension; and (e) adjusting the concentration of viral laden brain particles in the inactivated suspension to obtain the vaccine composition.

21. The process as defined in claim 20, wherein the amount of viral laden suckling mice or rat brain tissue material in the concentrated suspension in step (a) is from about 30 to about 60 percent by weight.

22. The process as defined in claim 20, wherein step (b) comprises subjecting the brain tissue material within the concentrated solution to high shear agitation.

23. The process as defined in claim 20, wherein the inactivating step (d) comprises combining the dilute suspension with an unhydrolyzed Beta propiolactone solution in an amount to provide a 1:1,000 to 1:10,000 dilution of Beta propiolactone in the combined product, and allowing the Beta propiolactone to hydrolize.

24. The process as defined in claim 23, wherein inactivation of the rabies virus is accomplished by maintaining said combined product at room temperature for a period of at least approximately 24 hours.

25. The process as defined in claim 24, wherein said combined product is periodically agitated during said period.

26. The process as claimed in claim 23, wherein said dilution of Beta propiolactone is approximately 1:2500.

27. The process as defined in claim 20, which further comprises the step of adding a preservatively effective amount of an antibiotic to the aqueous buffer solution.

28. The process as defined in claim 27, wherein the antibiotic is selected from the group consisting of penicillin, a streptomycin salt, amphotericin B and mixtures thereof.

29. The process as defined in claim 20, wherein step (c) comprises diluting the suspension to a concentration of brain tissue of from about 2 to about 10 percent by weight.

30. The process as defined in claim 20, wherein said step (c) comprises diluting the suspension to a concentration of brain tissue of from about 2.5 to about 6 percent by weight.

31. The process as defined in claim 20, wherein in step (e) the concentration of viral laden brain particles is adjusted to from about 2.5 to about 6 percent by weight.

32. The process as defined in claim 20, wherein in step (e) the concentration of viral laden brain particles is adjusted to from about 2.5 to about 3.5 percent by weight.

33. The process as defined in claim 20, wherein in step (e) the concentration of viral laden brain particles is adjusted to from about 5 to about 6 percent by weight.

34. The process as defined in claim 20, wherein the buffer composition comprises a mixture of tris (hydroxymethyl) amino methane and its hydrochloride.

35. The process as defined in claim 34, wherein the aqueous buffer solution is a 0.05 M solution of said buffer composition.

36. The process as defined in claim 20, which further comprises the following steps for preparing the viral laden suckling mice or rat brain tissue material:

(1) intracerebrally inoculating a batch of disease free suckling animals which are mice or rats at an age of from two to five days with a working seed containing living, fully virulent rabies virus;

(2) allowing the thus inoculated suckling animals to develop typical rabies symptoms and to become moribund; and (3) after a predetermined, minor percentage of the inoculated animals have died, withdrawing the viral laden brain tissue from the moribund animals.

37. The process as defined in claim 36, wherein step (3) comprises the steps of freezing the moribund animals for subsequent, further processing;

thawing a batch of the frozen animals; and withdrawing the viral laden brain tissue from the thawed animals.

38. The process as defined in claim 36, wherein said predetermined percentage of dead animals is from two to five percent of the inoculated animals.

39. The rabies vaccine composition as defined in claim 2, wherein the organic base is tris (hydroxymethyl) aminomethane, N-(2-hydroxyethyl) amino tris (hydroxymethyl) methane or N,N-bis (2-hydroxyethyl) amino tris (hydroxymethyl) methane.

* * * * *